(12) United States Patent
Olszanecki et al.

(10) Patent No.: US 8,686,037 B2
(45) Date of Patent: Apr. 1, 2014

(54) USE OF PIRACETAM FOR TREATING DIABETIC NEPHROPATHY

(75) Inventors: Rafal Olszanecki, Kraków (PL); Beata Bujak-Giżycka, Kraków (PL); Ryszard Korbut, Kraków (PL); Mariusz Gajda, Kraków (PL)

(73) Assignee: Uniwersytet Jagiellonski, Cracow (PL)

( * ) Notice: Subject to any disclaimer, the term of this patent is extended or adjusted under 35 U.S.C. 154(b) by 0 days.

(21) Appl. No.: 13/503,556

(22) PCT Filed: Oct. 23, 2010

(86) PCT No.: PCT/PL2010/050053
§ 371 (c)(1),
(2), (4) Date: Jun. 25, 2012

(87) PCT Pub. No.: WO2011/049475
PCT Pub. Date: Apr. 28, 2011

(65) Prior Publication Data
US 2012/0258997 A1    Oct. 11, 2012

(30) Foreign Application Priority Data
Oct. 23, 2009 (PL) .......................... 389364

(51) Int. Cl.
*A01N 37/06* (2006.01)
*A61K 31/22* (2006.01)

(52) U.S. Cl.
USPC ....................................... 514/549

(58) Field of Classification Search
None
See application file for complete search history.

(56) References Cited

U.S. PATENT DOCUMENTS 6,903,130 B1 * 6/2005 Lamberty et al. ............. 514/423
2008/0255093 A1 * 10/2008 Tam et al. ................ 514/217.01

FOREIGN PATENT DOCUMENTS

| EP | 1 356 812 A1 | 10/2003 |
| JP | 9 087178 A | 3/1997 |
| JP | 2003 226642 A | 8/2003 |
| WO | WO 01/39779 A1 | 6/2001 |
| WO | WO 02/089848 A2 | 11/2002 |

OTHER PUBLICATIONS

Winblad. Piracetam: a review of pharmacological properties and clinical uses. CNS Drug Reviews, vol. 11, No. 2, pp. 169-182.*
Malykh et al. Piracetam and piracetam-like drugs. Drugs, 2010, 70(3): 287-312.*
Winbald. Piracetam: a review of pharmacological properties and clinical uses. CNS Drug Reviews, vol. 11, No. 2. pp. 169-182. 2005.*
Kastelan S., "Ethics in drug treatment", Elsevier Science Publishers, Amsterdam, NL, 1994, XP002628729, Abstract.
Karie S. et al., "Nephrotoxicite des medicaments: veille bibliographique Jan. 2003-Dec. 2005", Nephrologie & Therapeutique, Elsevier, NL, vol. 2, No. 6, Nov. 2006, pp. 368-378.
Lebedeva, E.A., "Pharmacological blockade of protein glycosylation in diabetes mellitus with sulfonyl urea derivatives and biguanides", Chemical Abstract Service, Columbus, Ohio, US, Feb. 1997, XP002628731, Abstract.
Nalbandian, R.M. et al., "Erythrocyte-Endothelial Cell Adherence In Sickel Cell Disease, Diabetes Mellitus, And Falciparum Malaria: Adverse Effects Reversewith Piracetam", Medical Hypotheses, Eden Press, Penrith, US, vol. 8, No. 2, Feb. 1982, pp. 155-162.
Ozczn M. et al., "Antinociceptive efficacy of levetiracetam in a mice model for painful diabetic neuropathy", ACTA Anaesthesiologica Scandinavica, vol. 52, No. 7, Aug. 2008, pp. 926-930.
International Search Report issued by the International Searching Authority (ISA/O.E.P.M.) on Mar. 17, 2011 in connection with International Application No. PCT/PL2010/050053.

* cited by examiner

*Primary Examiner* — Anna Pagonakis
(74) *Attorney, Agent, or Firm* — Gary J. Gershik; Cooper & Dunham LLP

(57) ABSTRACT

The invention is related to the new application of selected derivatives of 2-pyrrolidone to inhibition of protein glycation and to prevention and treatment of diabetes complications, such as atherosclerosis, nephropathy, retinopathy, cataract or neuropathy.

2 Claims, 3 Drawing Sheets

USE OF PIRACETAM FOR TREATING DIABETIC NEPHROPATHY

Figure 1:
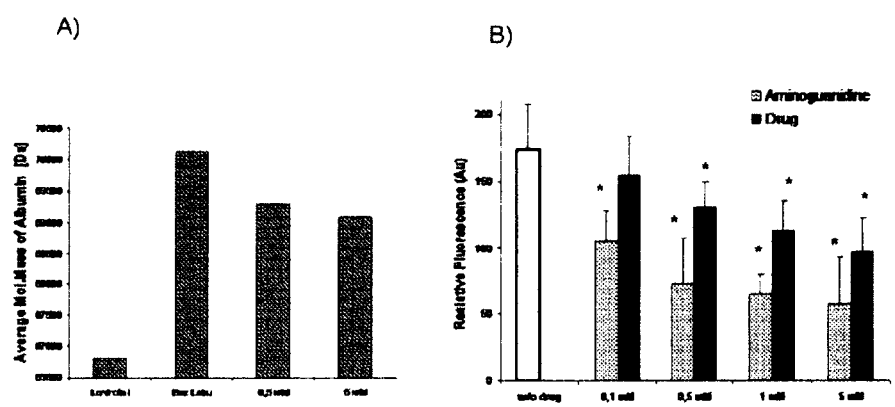

This application is a §371 national stage of PCT International Application No. PCT/PL2010/050053, filed Oct. 23, 2010, designating the United States and claiming priority of Polish Patent Application PL 389364, filed Oct. 23, 2009, the contents of all of which are hereby incorporated by reference into this application.

The invention relates to new application of known substances in medicine. In particular, it relates to the use of 2-pyrrolidone derivatives (racetams) for the inhibition of protein glycation.

Diabetes and its complications are one of the major health problems in the social scale. Hyperglycemia is the main factor responsible for the organ damage in diabetes. Glucose spontaneously reacts with the free amino groups of lysine in proteins and forms Schiff base, which undergoes further transformations. This cascade of reactions is called non-enzymatic Maillard reaction and its products, produced on particular stages of this process, are responsible for atherosclerosis, nephropathy, retinopathy, cataract or neuropathy.

Glycation of proteins is a multistep process. The first step (so-called early stage of glycation) is a nucleophilic addition reaction between free amino group ($-NH_2$) of protein at the N-terminus or at ε-amino group of lysine side chain and carbonyl group of the reduced form of glucose, which results in an unstable product—the Schiff's base, which undergo Amadori rearrangement to give a stable ketoamine—so-called Amadori product. In the next step, Amadori product undergo further oxidation and dehydratation and is degraded, via enol form, to various free carbonyl compounds (such as glyoxal, methylglyoxal or 3-deoxyglucosone), which are much more reactive than sugars. These dicarbonyl compounds, called propagators, participate in formation of Advanced Glycation End-products (AGEs). Propagators via reactions of oxidation, dehydratation and cyclization react with free amino groups of proteins and produce stable yellow-brown, often fluorescent, insoluble compounds—AGEs. AGEs can accumulate in long-lived proteins, and are widely recognized as responsible for organ damage in diabetes, e.g. by stimulation of specific receptors on the cells' surface (RAGE).

It has been shown that prevention of AGEs formation by use of drugs—protein glycation inhibitors—may reduce either the incidence or severity of organ damage in animal models of diabetes; similar effect has been noted in preliminary clinical studies.

However, effective and safe inhibitors of glycation are still lacking. Studies of known strong inhibitors, such as aminoguanidine (Pimagedine, Alteon Inc.), or ALT-711 (alagebrium chloride, Synvista Therapeutics Inc.), revealed side effects, which significantly limited the use of aminoguanidine or led to suspension of clinical trials with alagebrium. It should be noted that due to non-enzymatic character of glycation, potential inhibitors should be present near the target protein at high concentrations, what implicates high dosage and increased risk of adverse effects. Thus, there is a strong need to identify drugs which could be effective in the treatment of diabetes complications and could inhibit the glycation of proteins with minimal risk of adverse effects.

The aim of present invention is to demonstrate the ability to inhibition of glycation of proteins by widely known and safe drug, used in the clinic due in other indications at doses that allow to achieve tissue concentrations of several hundreds micromols to few milimols per liter.

The invention relates to the application of known drug, 2-(2-oxo-1-pyrrolidin-1-yl) acetamide, with common name piracetam, in a new therapeutic indication.

As it is known from previous publications, piracetam influences energy metabolism of cells in central nervous system, increasing their use of oxygen and glucose. This results in facilitatation of the synthesis of high-energy compounds and increased energetic reserve. Among other actions, piracetam augments the ability of neurons to synthesize neurotransmitters which improves the metabolism of the central nervous system. Piracetam is mainly used in syndrome of deterioration of brain functions due to inflammation, stroke, shock and surgical operations—especially after neurosurgery procedures.

N-substituted lactams and obtaining thereof, as well as their application in medicine, e.g. for the treatment of movement disorders were described in the U.S. Pat. No. 3,459,738. Other pharmacologicaly useful compounds, N-substituted aminealkyl-2-oxo-1-pyrrolidine acetamides, were disclosed in U.S. Pat. No. 4,145,347; the way of obtaining thereof in reaction of 2-oxo-1-pyrrolidine acetate ester with proper amine was also described.

A method of synthesis of 2-oxo-1-pyrrolidineacetamide or piracetam was also disclosed in Canadian Pat. No. 1059137. In U.S. Pat. No. 7,217,826 new derivatives of 2-oxo-1-pyrrolidine or their salts, useful in the treatment of neurological disorders, such as epilepsy were described. This invention relates to derivatives of 2-oxo-1-pyrrolidine, obtaining thereof and their medical use. A method of synthesis of formation of alpha-ethyl-2-oxo-1-pyrolydineacetamide and its derivatives from unsaturated derivatives of 2-oxo-1-pyrrolidine was described.

In the patent application No. P 357472, based on priority of EP 99 99123803 and EP 99 99124269, an application of (S)-(−)-α-ethyl-2-oxo-1-pyrrolidineacetamide to production of neuronal activity inhibitor was disclosed, as well as new pharmaceuticals containing (S)-(−)-α-ethyl-2-oxo-1-pyrrolidineacetamide. The application of levetiracetam to treatment of bipolar disorder, mania and neuropathic pain was described.

The present invention relates to the new application of 2-pyrrolidone derivative to inhibition of protein glycation, and the derivative is selected from the group consisting of:
a. compound with general formula I:

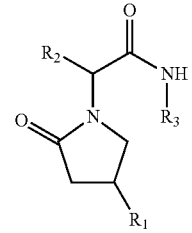

formula I in which R1, R2 are: hydrogen atom or halogen atom or amino group ($-NH_2$), hydroxyl group ($-OH$), linear or branched $C_{1-5}$ alkyl groups, linear or branched $C_{1-4}$ alkyl-amino groups or guanidine group, R3 is: hydrogen atom or halogen atom or amino group ($-NH_2$), hydroxyl group ($-OH$), linear or branched $C_{1-5}$ alkyl groups, linear or branched $C_{1-4}$ alkyl-amino groups or Another subject of the invention is application of 2-pyrrolidone derivative to production of drug for the prevention or treatment of diabetes complications, in which the derivative is selected from the group consisting of:

a. compound of general formula I:

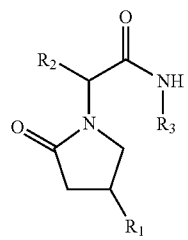

formula I in which R1, R2 are: hydrogen atom or halogen atom or amino group (—NH$_2$), hydroxyl group (—OH), linear or branched C$_{1-5}$ alkyl groups, linear or branched C$_{1-4}$ alkyl-amino groups or guanidine group, R3 is: hydrogen atom or halogen atom or amino group (—NH$_2$), hydroxyl group (—OH), linear or branched C$_{1-5}$ alkyl groups, linear or branched C$_{1-4}$ alkyl-amino groups or guanidine group, phenyl group (C$_6$H$_5$—) or phenyl group substituted by one or more hydroxyl, methyl, amino, alkylamino groups or halogen atoms, b. compound of general formula II:

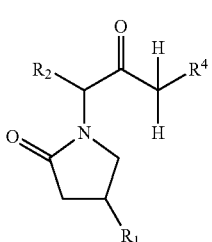

formula II in which R1, R2 mean as above, while R4 is C$_6$H$_4$—OCH$_3$ group.

c. compound of general formula III:

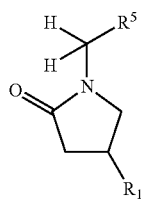

formula III in which R1 means as above, while R5 is C$_6$H$_5$ group.

Preferably, according to the invention, the 2-pyrrolidone derivative used is selected from the group comprised of: piracetam, oxiracetam, levetiracetam, brivaracetam, pramiracetam, nefiracetam, aniracetam or nebracetam.

Above mentioned drugs were described in the literature and are presented in Table 1.

TABLE 1

| R1 | R2 | R3 | R4 | R5 | International name |
|---|---|---|---|---|---|
| H | H | H | | | Piracetam (formula I) |
| OH | H | H | | | Oxiracetam (formula I) |
| H | Et (CH$_2$CH$_3$) | H | | | Levetiracetam (formula I) |
| CH$_2$CH$_2$CH$_3$ | Et (CH$_2$CH$_3$) | H | | | Brivaracetam (formula I) |
| H | H | CH$_2$CH$_2$N(CH(CH$_3$)$_2$)$_2$ | | | Pramiracetam (formula I) |
| H | H | C$_6$H$_4$(CH$_3$)$_2$ | | | Nefiracetam (formula I) |
| H | H | | C$_6$H$_4$—OCH$_3$ | | Aniracetam (formula II) |
| NH$_2$ | | | | C$_6$H$_5$ | Nebracetam (formula III) | guanidine group, phenyl group (C$_6$H$_5$—) or phenyl group substituted by one or more hydroxyl, methyl, amino, alkylamino groups or halogen atoms, b. compound of general formula II:

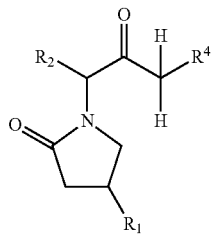

formula II in which R1, R2 mean as above, while R4 is C$_6$H$_4$—OCH$_3$ group.

c. compound of general formula III:

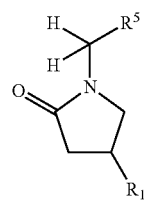

formula III in which R1 means as above, while R5 means $C_6H_5$ group.

Preferably, according to the invention, the 2-pyrrolidone derivative used is selected from the group comprised of: piracetam, oxiracetam, levetiracetam, brivaracetam, pramiracetam, nefiracetam, aniracetam or nebracetam.

Of particular benefit is also application of any of the above-mentioned 2-pyrrolidone derivatives for prevention or treatment of any of the diabetes complications such as atherosclerosis, nephropathy, retinopathy, cataract or neuropathy.

Figure 2:
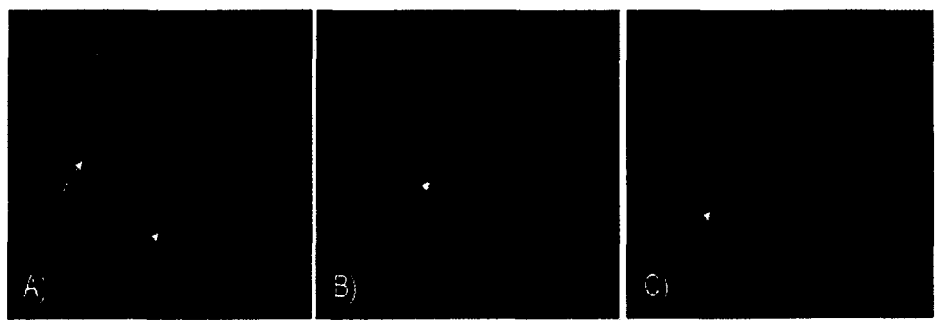

The subject of invention as an embodiment is illustrated on FIG. 1, which shows:
A) influence of examined compound on gain of molecular weight of albumin (50 mg/ml) incubated with glucose (0.5 M) for 4 weeks,
B) influence of examined compound and aminoguanidine on glycation-dependent fluorescence of albumin incubated with glucose (0.5 M) for 4 weeks (n=4).
* p<0.05 t-Student test FIG. 2 illustrates influence of examined compound on the degree of protein glycation in renal glomeruli of rats in model of streptozotocin-induced diabetes (8 weeks).
Red fluorescence is related to binding of specific antibody to glycated proteins.
A—control rat kidney (without diabetes),
B—kidney of diabetic rat,
C—kidney of diabetic rat treated with examined compound.
Arrows indicate renal glomeruli. The images are representative for n=3 animals.

Figure 3:
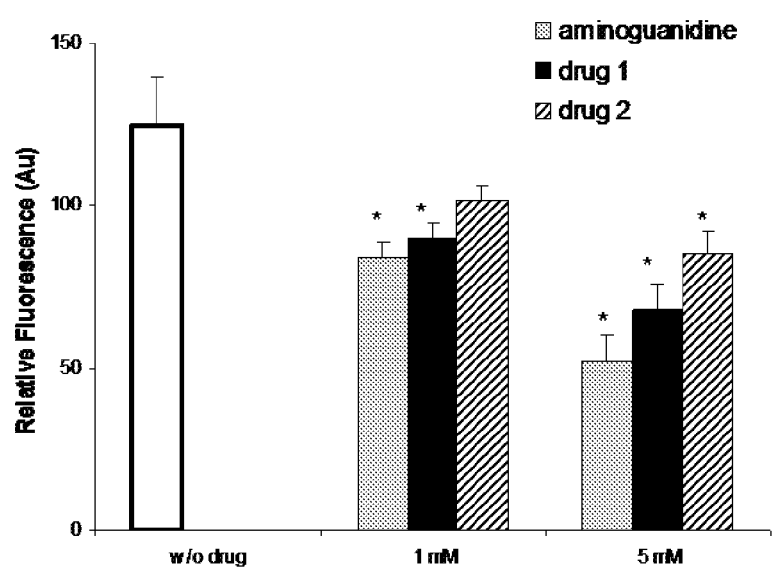

FIG. 3 shows comparison of influence of two 2-pyrrolidone derivatives (drug 1—piracetam; drug 2—levetiracetam) and aminoguanidine on glycation-dependent fluorescence of albumin incubated with glucose (0.5M) for 4 weeks (n=4).
* p<0.05 t-Student test

EXAMPLES

In Vitro Experiments

Example No 1

To test the potency of glycation inhibiting action of examined drug two independent methods were used: mass spectrometry and spectrofluorimetic method, showing relative action of tested drug compared to the effect of known, potent glycation inhibitor—aminoguanidine hydrochloride.

Glycation of protein in vitro was carried out according to following scheme:
50 mg of protein (albumin, myoglobin) was dissolved in 1 ml 0.01M PBS (pH 7.4), containing D-glucose (0.1; 0.3; 0.5; 1M) and 5 mM toluene (as a bacteriostatic compound). The examined drug or aminoguanidine hydrochloride were added to samples at final concentrations from 0.1 mM to 5 mM. Samples were incubated at 37° C., in dark, for a specified period of time (1, 2, 3 and 4 weeks). Then, the protein was concentrated by ultrafiltration (30 min at 4000×g, 16° C.) with Amicon 50 cartridges (Millipore) with cut-off of 50 kDa (in case of albumin) or Amicon 10 cartridges with cut-off of 10 kDa (in case of myoglobin). The concentrated protein samples were dialyzed for 24 hrs, against distilled water, using dialysis membranes: Spectra Por (cut-off of 50 kDa for albumin and cut-off of 12-14 kDa for myoglobin). Then the samples were lyophilized overnight.
Control samples were prepared as above except of addition of glucose (control I) or drugs (control II).

Example No 2

Measurement of Glycation by Mass Spectrometry

The method is based on a measurement of protein molecular weight (albumin, myoglobin), which is increased in proportion to the number of bound sugar moieties. The action of drug—an inhibitor of glycation—is expressed the degree of inhibition of increase of protein molecular weigh.
Lyophilized samples of proteins were enzymatically digested: 1 mg of protein was dissolved in 1.3 ml of 50 mM ammonium hydrocarbonate buffer (pH 8.3). In order to break disulfide bonds 150 of DTT (45 mM) was added and the samples were heated at 60° C. for 1 hour. After cooling to the room temperature, in order to prevent formation of disulfide bonds, 20 µl of 55 mM IAA was added to the each sample; then they were kept for 30 min in the dark place. Then freshly-prepared solution of trypsin (200 µl, 100 ng/ml in water) was added and the mixture was incubated at 37° C. overnight. The next day reaction was stopped by adding 5 µl of concentrated formic acid. Samples containing myoglobin were prepared similar way, however with omitting the steps with disulfide bond breakage and block of cysteins by IAA (myoglobin molecule does not contain cystein residues).

Mass spectrometric detection was performed using a LCQ ion-trap mass spectrometer (Finnigan, San Jose, USA), equipped with an ESI source (electrospray ionization). The main working parameters were as follows: sheath gas (nitrogen) flow rate 60 psi, ion spray voltage 4.5 kV, capillary temperature 200° C. 1 mg of lyophylized protein was dissolved in 1 ml of 0.2% formic acid in methanol/water (50/50). Directly before injection to the mass spectrometer sample was diluted 10 times with 0.1% formic acid. Based on obtained MS spectra, average protein molecular weight was calculated using BioWorks 1.0 software (Finnigan, San Jose, USA).

Separation of peptides was performed on a reversed-phase, high performance liquid chromatography (HPLC) system using PepMap 100 C18 column (150 mm×1 mm ID, 5 µl m particle size) (LC Packings, Dionex Comp., USA) with linear gradient:
A—0.1% formic acid in water and acetonitrile (95:5) (phase A)
B—0.1% formic acid in water and acetonitrile (5:95) (phase B).
at a flow rate of 45 µl/min.
Mass detection was carried out in the Triple Play mode (full scan; MS/MS and zoom scan). In order to determination of sequence of peptides and possible modifications of aminoacid residues the MS data were analyzed by X!tandem (the Global Proteome Machine Organization).

Example No 3

Measurement of Albumin Glycation Using Spectrofluorimetric Method

Sugar residues are characterized by fluorescence—Ex/Em 370/440 nm The action of drug is expressed by a suppression of the intensity of fluorescence.

Lyophylized protein samples were dissolved in 0.01M PBS (pH 7.4), at concentration 0.5 mg protein/1 ml of buffer. Measurements were carried out using Perkin Elmer LS 50B spectrofluorimeter. Fluorescence intensity was measured at 440 nm emission upon excitation of 370 nm.

In Vivo Experiments

Example No 4

All experimental studies using animals were approved by an Ethical Committee at the Jagiellonian University. Diabetes model was established by the single, intraperitoneal administration of streptozotocin (STZ, 75 mg/kg in citrate buffer, pH 4.5) to three-month Sprague-Dawley rats. In order to maintain glycaemia between 350 and 450 mg/dL, animals were treated twice a week by insulin (neutral protamine Hagedorn, NPH, 2-3 U/300 g of body weight).

The rats were divided into three groups (each one of n=4 animals): "control" group—animals injected with citrate buffer only (sham animals), "diabetes" group—STZ treated animals and "STZ+drug" group—STZ-rats treated with examined drug (354±40 mg/kg/day in drinking water). The experiment lasted 8 weeks. Animals were anesthetized and killed, and both the tissue samples (kidneys, heart, lungs, brain) as well as blood samples were harvested. The presence of AGEs was evaluated by immunohistochemistry, with use of specific antibodies (Abcam, USA).

Results

In in vitro model, examined drug, inhibited dose-dependently addition of glucose moieties to albumin, with a strength comparable to known, strong inhibitor of glycation-aminoguanidine (FIG. 1). As evidenced by mass spectrometry method, at concentration of 5 mM, tested compound inhibited protein glycation by 33% (as compared to the mass of albumin incubated with glucose alone) (FIG. 1A). At concentration of 5 mM, tested compound inhibited glycation by 45% (at the same concentration aminoguanidine inhibited glycation by 67%), as evidenced by spectrofluorimetric method. (FIG. 1B).

The tested drug did not influence glycaemia in rats injected with STZ (429±65.0 vs. 399±42.8 mg/dL). In immunohistochemistry for AGEs, the drug significantly reduced both the number of AGE-positive glomeruli and the severity of changes in glomeruli (FIG. 2).

To conclude, examined drug inhibited protein glycation both in vitro and in vivo at the concentration similar to known inhibitors of glycation.

The invention claimed is:

1. A method of treating diabetic nephropathy in a subject suffering from diabetes, comprising administering piracetam to the subject in an amount effective to treat diabetic nephropathy so as to thereby treat diabetic nephropathy in the subject.

2. The method of claim 1, consisting of administering piracetam to the subject in an amount effective to treat diabetic nephropathy so as to thereby treat diabetic nephropathy in the subject.

* * * * *